United States Patent [19]
Okamoto et al.

[11] Patent Number: 5,087,767
[45] Date of Patent: Feb. 11, 1992

[54] METHOD FOR PREPARING BISPHENOL A

[75] Inventors: Kenichi Okamoto; Hidetoshi Kita, both of Yamaguchi; Yasuo Tanaka, Tokyo; Shigeru Iimuro, Aichi, all of Japan

[73] Assignee: Mitsui Toatsu Chemicals, Inc., Tokyo, Japan

[21] Appl. No.: 630,814

[22] Filed: Dec. 20, 1990

[30] Foreign Application Priority Data

Dec. 25, 1989 [JP] Japan .................................. 1-332802

[51] Int. Cl.⁵ ........................ C07C 39/16; C07C 37/20
[52] U.S. Cl. .................................. 568/727; 568/722; 568/724; 568/728
[58] Field of Search ............... 568/722, 727, 728, 724, 568/749

[56] References Cited

U.S. PATENT DOCUMENTS

| 2,572,141 | 10/1951 | Harris | 568/727 |
| 2,884,462 | 4/1959 | Henry | 568/722 |
| 4,777,301 | 10/1988 | Olson | 568/727 |

FOREIGN PATENT DOCUMENTS

| 489747 | 6/1976 | Australia | 568/749 |
| 0264113 | 4/1988 | European Pat. Off. | 568/749 |
| 0321569 | 6/1989 | European Pat. Off. | 568/749 |
| 2418975 | 10/1975 | Fed. Rep. of Germany | 568/727 |
| 61-1078741 | 4/1986 | Japan | 568/727 |

OTHER PUBLICATIONS

Patent Abstracts of Japan, vol. 10, No. 252 (C-369)(2308), 08/29/86; JP-A-6178741.

Primary Examiner—Werren B. Lone
Attorney, Agent, or Firm—Burns, Doane, Swecker & Mathis

[57] ABSTRACT

A method for preparing 2,2-bis(4-hydroxyphenyl)propane comprises reacting acetone and phenol in the presence of an acidic ion-exchange resin as a catalyst wherein the reaction of acetone and phenol is performed while removing a part of the water generated during the reaction from a mixed solution containing acetone and phenol by a pervaporation method. According to the method, the water generated through the reaction can rapidly be removed simultaneously with or alternatively to the reaction by a pervaporation operation and, therefore, the catalytic activity of the ion-exchange resin is not impaired at all. Moreover, any complicated operations associated with the dehydration are not required. Thus, the acidic ion-exchange resin catalyst can continuously be used over a long time period without any treatment for the regeneration thereof. Further, according to the method, bisphenol A can be economically prepared from acetone and phenol in a high conversion rate and high yield.

14 Claims, 1 Drawing Sheet

METHOD FOR PREPARING BISPHENOL A

BACKGROUND OF THE INVENTION

1. Field of the Invention

The present invention relates to a method for preparing highly pure 2,2-bis(4-hydroxyphenyl)propane (hereinafter referred to as "bisphenol A").

More specifically, the present invention pertains to a method for preparing bisphenol A which comprises reacting phenol and acetone in the presence of an acidic ion-exchange resin as a catalyst and which is characterized in that the reaction is performed while a part of the water generated during the reaction is removed from the reaction mixture containing phenol and acetone through a separating membrane.

2. Description of the Prior Art

Bisphenol A has been used as a starting material for producing polycarbonate resins and epoxy resins and recently demands thereof as a starting material for preparing engineering plastics or the like has gradually been increased.

It has been known that highly pure bisphenol A must be used in such applications. In particular, when it is used as a starting material for polycarbonate resins, bisphenol A must be colorless and highly pure. On the other hand, a method for economically producing bisphenol A has been desired as the demands thereof increased.

Bisphenol A has been prepared by reacting acetone with an excess of phenol in the presence of an acidic catalyst and optionally a co-catalyst such as a sulfur compound. The reaction may be batchwise or continuously performed.

As such catalysts in this condensation reaction, there have generally been used those catalysts soluble in the reaction system such as hydrochloric acid or sulfuric acid. However, the use of apparatus of an expensive material is required in order to use these corrosive acidic catalysts and these catalysts (acids) must be removed from the reaction mixture through a large scale purification process. This makes these methods economically unfavorable. Moreover, the quality of the resulting product is greatly impaired even if a trace amount of these acids remains in the product.

A solid acidic catalyst may be employed as a catalyst for preparing bisphenol A. When such a solid acidic catalyst is used, the foregoing problem of corrosion can be solved to some extent. Moreover, this results in the simplification of the production process since a reactor equipped with a fixed bed or a fluidized bed as the catalyst layer can be adopted and correspondingly the complicated process for removing the catalyst can be omitted unlike the cases wherein a soluble catalyst is employed.

It has been known that acidic ion-exchange resin can be used as such a solid acidic catalyst (see, for instance, Japanese Patent Examined Publication (hereunder referred to as "J.P. KOKOKU") No. Sho 36-23334).

The reaction can be accelerated by the addition of a co-catalyst such as a sulfur atom-containing compound, e.g., those carrying a mercapto group even when an ion-exchange resin is employed as the catalyst (see J.P. KOKOKU No. Sho 46-19953). In this case, the mercapto group is fixed to the ion-exchange resin in the form of a compound having a nitrogen atom on the side opposite to the mercapto group. In these methods, the reaction is performed using phenol in an amount of 4 to 10 times the molar amount of acetone at a temperature ranging from 40° to 100° C. and the ion-exchange resin is dried prior to use since the lower water content of the reaction system is preferred.

The method for preparing bisphenol A from acetone and phenol in the presence of an ion-exchange resin catalyst suffers from a problem that the catalytic activity of the ion-exchange resin is greatly influenced by the water formed almost stoichiometrically during the reaction with the formation of the desired product, bisphenol A, irrespective of whether the ion-exchange resin is modified with an amine carrying a mercapto group or not.

The amount of the water generated during the reaction reaches not less than 1.4% at the time when the acetone conversion reaches 50% even if the reaction is performed at a molar ratio, phenol/acetone, of 6:1.

For this reason, the reduction in the catalytic activity of the ion-exchange resin due to the presence of water formed starts as soon as the reaction is initiated even if the ion-exchange resin catalyst has been dried prior to use.

Moreover, if a mineral acid catalyst soluble in phenol such as hydrochloric acid or sulfuric acid is employed, the acetone conversion generally reaches 95% or more within 6 to 8 hours. On the other hand, if an ion-exchange resin catalyst is used, the reaction rate is gradually lowered since the amount of water present in the reaction system increases as the reaction proceeds. As a result, it takes 10 hours or more to achieve a conversion of 95% or more in the batch reaction system even if a large amount of a catalyst is employed and it is substantially impossible to achieve a conversion of the order of 95% or more in the continuous reaction system.

Therefore, if a fixed bed of an ion-exchange resin is used, the problems associated with the case wherein a soluble inorganic acid catalyst is used such as the removal of the catalyst from the reaction system and the contamination of the remaining acid and/or inorganic substances into the result product can be solved, but the use of the fixed bed of the resin suffers from the problems such as the lowering of the reaction rate due to the water generated through the reaction, the corresponding lowering of the acetone conversion and the necessity of complicated processes associated with post-treatment.

If it is intended to increase the acetone conversion up to 90% or higher according to a conventional technique in which a fixed bed system is adopted, a large amount of an ion-exchange resin must be employed. This is unpracticable from the industrial viewpoint.

Accordingly, it is stated in J.P. KOKOKU No. Sho 36-23334 that the conversion of acetone is preferably about 50%. In this patent, the unreacted acetone is separated from the reaction system together with a part of the water generated and a part of phenol and then isolated through complicated processes which require a large amount of separation energy for recovering and reusing it.

However, the concentration of bisphenol A in the resulting flow of the reaction product is low if such a method is adopted and the method in turn requires excess energy for the separation and purification of the product and is not considered to be an economically effective process.

Alternatively, a method is also known which comprises the steps of removing acetone, water and a part of phenol from a part of the flow of the reaction product and recycling a part thereof to the reaction system to thus increase the concentration of bisphenol A in the flow of the reaction product (see Japanese Patent Unexamined Publication (hereunder referred to as "J.P. KOKAI") No. Sho 54-19951), but any means for recovering the unreacted acetone is not disclosed in the patent, the throughput capacity of the reactor is substantially impaired in this method and, therefore, this is not an economically effective method.

J.P. KOKOKU No. Sho 63-52021 discloses a method for preparing bisphenol A which is characterized in that the reaction is peformed while a mixed solution containing phenol and acetone is simultaneously or alternatively brought into contact with an acidic ion-exchange resin and a dehydrating agent. According to this method, the acetone conversion can be increased to almost 100% without recycling the flow of the reaction product. However, the dehydrating agent must, in any case, be regenerated before the dehydrating agent is saturated with the water formed during the reaction and, therefore, this method requires the use of a large-scale apparatus and complicated operations in order to carry it out on an industrial scale.

SUMMARY OF THE INVENTION

Accordingly, an object of the present invention is in general to provide a method for eliminating the foregoing drawbacks encountered when bisphenol A is prepared from a mixed solution containing acetone and phenol in the presence of a solid acid, in particular an acidic ion-exchange resin as a catalyst and more specifically to provide a method for preparing bisphenol A which makes it possible to inhibit the reduction in the catalytic activity due to the water generated during the reaction, to enhance the acetone conversion and to simplify the post-treatment processes of the reaction product.

The inventors of this invention have conducted intensive studies to achieve the foregoinq object of the invention, have found out that it is effective to perform the reaction while a part of the water generated during the reaction is removed through a pervaporation method and thus have completed the present invention.

According to an aspect of the present invention, there is provided a method for preparing bisphenol A (2,2-bis(4-hydroxyphenyl)propane) which comprises reacting acetone and phenol in the presence of an acidic ion-exchange resin as a catalyst wherein the method is characterized in that the reaction of acetone and phenol is performed with simultaneous removal of a part of the water generated during the reaction from a mixed solution containing acetone and phenol by a pervaporation method.

DESCRIPTION OF THE PREFERRED EMBODIMENTS

Figure 1:
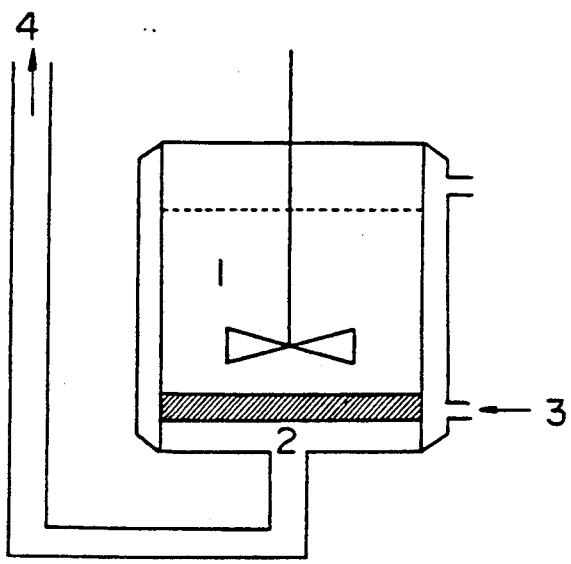
FIGS. 1 and 2 are schematic diagrams for illustrating preparation apparatuses used in Examples 1 and 2 respectively.

In the method of the present invention, the pervaporation method for separating water is performed by the use of a separating membrane selective toward water which is selected from inorganic porous membranes, organic polymer membranes and/or inorganic-organic composite membranes.

The inorganic porous membrane is at least one member selected from the group consisting of porous glass membranes, porous silica membranes, porous alumina membranes and porous ceramics membranes and the organic polymer membrane is at least one member selected from the group consisting of ionized polysaccharide membranes, ion-exchange membranes of styrene-divinylbenzene resins or perfluoro resins, polyamide membrane, polyimide membranes, polyamidoimide membranes, polyvinyl alcohol membranes, polyvinyl acetate membranes and polyacrylonitrile membranes.

In addition, the inorganic-organic composite membrane is those comprising at least one organic polymer membrane selected from those listed above which is supported by at least one inorganic porous membrane listed above.

The method of the present invention can be performed in either batchwise and continuous reactors. When a continuous reactor is used, one or at least two reactors which are arranged in series or in parallel may be used. If at least two reactors connected in series are used, the starting material is supplied only to the first reactor or alternatively it may be supplied to the second reactor and the reactors subsequent thereto in portions. In particular, acetone is preferably supplied in portions according to the latter method.

In the method wherein acetone is supplied in portions, the acetone concentration during the reaction can be reduced to thus inhibit the production of by-products, but a larger reactor must be used, the reaction rate is correspondingly lowered and the amount of the unreacted acetone increases.

On the contrary, the method of the present invention makes it possible to convert the acetone thus supplied into bisphenol A in a high conversion and to hence substantially increase the concentration of bisphenol A in the resulting solution containing the reaction products.

The reaction and the dehydration are simultaneously or alternatively performed. When the batchwise or continuous reaction is carried out in one reactor, the reaction and the dehydration are preferably carried out simultaneously. On the other hand, if at least two reactors are employed, the reaction and the dehydration may be simultaneously or alternatively performed depending on the shape of the pervaporation membrane used, but preferably they are simultaneously performed.

The resin used as a catalyst in the method of the present invention is a sulfonic acid type cation-exchange resin which is modified with a compound carrying a mercapto group in the molecule. The sulfonic acid type cation-exchange resin may be, for instance, commercially available styrene-divinylbenzene resins or perfluoro resins which are well-known. Moreover, the modification of the resin with a compound having a mercapto group is the known technique and examples of such compounds are mercaptoalkylamines (J.P. KOKOKU No. Sho 46-19953), thiazolidine compounds (J.P. KOKAI No. Sho 48-71389) and pyridinealkanethiol compounds (J.P. KOKAI No. 57-35533).

The ratio of modification of the resin in general ranges from 5 to 35 mole %, preferably 10 to 20 mole % with respect to the molar amount of the sulfonic acid groups in the resin. This is because, if the rate of modification is too low, the reaction rate is lowered and the amount of Dianin's compound formed increases, while if it is too high, both the reaction rate and the rate of conversion are lowered.

The modification of the resins may be batchwise performed according to the method disclosed in J.P. KOKOKU No. Sho 46-19953 or may be carried out by forming a fixed bed of a non-neutralized resin and then passing a solution of mercaptoamine through the fixed bed to thus give a fixed bed which is partially modified as disclosed in J.P. KOKAI No. Sho 53-14680.

The acidic ion-exchange resin catalyst used in the method of the present invention is preferably dried prior to use, but it is not necessarily in the dry state. Regardless of a slight decrease in the conversion speed and the rate of conversion observed immediately after starting the reaction, the water present in the reaction solution is immediately discharged outside the reaction system through the separating membrane and correspondingly the water content in the resin catalyst is maintained low. Thus, the conversion speed and the rate of conversion comparable to those achieved when a dried resin catalyst is employed can be ensured.

The separating membrane used in the method of the present invention must be permeable toward water as much as possible, but as impermeable to acetone, phenol and bisphenol A as possible. The separating membrane preferably has a water permeation rate of from 10 to 10,000 g/m$^2$ h and a ratio of water-permeation rate to (acetone+phenol)-permeation rate (hereunder referred to as "water/(acetone+phenol)") of not less than 50.

The reaction between acetone and phenol is an exothermic reaction and, therefore, the reaction must be performed with heating for achieving an economically acceptable reaction rate. Thus, the separating membrane must be heat resistant. The separating membrane may be obtained from any material so long as the materials used satisfy the foregoing requirement.

Examples of such materials include inorganic porous membranes having a fine pore size of 20 to 10 Å which can effectively separate water from acetone. Examples of the inorganic porous membranes of this type further include porous glass obtained by making use of the phase inversion phenomenon of sodium borosilicate glass as well as porous silica or alumina membranes obtained according to the solgel method. These membranes may be used alone or may be supported by a porous ceramics having a greater pore size and then put into practical use.

Examples of organic polymeric materials for producing the organic polymer membranes include ionized polysaccharide membranes such as cellulose, chitin chitosan, alginic acid and chondroitin sulfate membranes; ion-exchange resin membranes of styrene-divinylbenzene resins or perfluoro resins; and polymer membranes such as polyamide membranes, polyimide membranes, polyamidoimide membranes, polyvinyl alcohol membranes, polyvinyl acetate membranes and polyacrylonitrile membranes. These organic polymer membranes may be those conventionally known or may be those conventionally known which are modified by introducing functional groups such as hydroxyl, carboxyl and/or sulfonic acid groups into them or those which are modified by introducing compounds carrying these functional groups into their main chain, side chains and/or chain ends, for further enhancing the water-permeability thereof. The organic polymer membrane may have cross-linked structure for suppressing the swelling of the membranes and for improving the strength of the membranes.

Moreover, the foregoing organic polymer membrane may be supported by an inorganic membranes such as porous silica membrane, a porous alumina gel membrane or a porous ceramics membrane to thus give an inorganic-organic composite membrane in order to impart, to the organic polymer membranes, a strength capable of withstanding industrial continuous use.

These membranes may be used in combination of two or more irrespective of the kinds of the membranes (i.e., they may be either or both of organic and inorganic membranes).

These membranes may have any form such as sheet-like form, tubular form or hollow fiber form or further may be an organic-inorganic composite membrane such as an inorganic membrane carrying a polymer membrane thereon.

The catalyst can be positioned on a sheet-like membrane, in a tubular membrane or outside a hollow fiber.

In the method of this invention, acetone is reacted with phenol, phenol is used in an amount ranging from 3 to 20 times, preferably 4 to 12 times the molar amount of acetone and any solvent as a third component is not substantially used in this reaction. If the reaction is performed in two or more reactors continuously arranged, the molar ratio of unreacted phenol to acetone in each reaction zone is desirably not less than 5.

The molar ratio of the reaction can be determined on the basis of the relation between the temperature of the flow discharged at the final reaction stage and the desired concentration of bisphenol A. If the concentration of bisphenol A is too high, it forms, in the reaction zones, a crystalline adduct with phenol which makes the continuous operation difficult. On the other hand, if it is too low, the separation requires a great deal of useless energy.

Preferably, the ratio of phenol to acetone ranges from 20 to 15 at a reaction temperature of 60° C., and 6 to 4 at 100° C.

If acetone is supplied to two or more reaction zones in portions, the molar ratio of unreacted phenol to acetone at the inlet of each reaction zone is preferably not less than 10. This leads to the substantial reduction in the amount of by-products.

The reaction temperature may arbitrarily be selected as long as it is not detrimental to the ion-exchange resin catalyst and the separating membrane. The reaction temperature suitably ranges from 30° to 120° C. and preferably 50° to 100° C. This is because, if the reaction temperature is too low, the reaction rate is low, while if it is too high, the amount of by-products formed is increased. The reaction zones may, if necessary, be heated or cooled. The reaction time varies depending on the manner of the reaction, in particular the reaction temperature. For instance, the reaction time generally ranges from 0.1 to 10 hours for a batchwise reaction in which a reaction vessel provided with a stirring machine is used and it is adjusted so that the space velocity (S.V.) is controlled to 0.1 to 10/HR for a piston-flow continuous reaction with a fixed bed catalyst.

The method of the present invention will be explained in more detail with reference to the attached drawings. The starting materials, acetone and phenol, are introduced into a reactor 1 and an ion-exchange resin as a catalyst is charged therein. A part of the wall of the reactor (the bottom portion in FIG. 1 or the external wall of a pressure reducing tube in FIG. 2) is constructed by a selective separating membrane 2 according to the present invention. The internal temperature of the reactor is controlled by water 3 circulated along the external wall of the reactor. The water generated in the reactor through the reaction is discharged outside the reaction system by externally reducing the pressure therein. The attached figures are given for explaining the effect of the present invention by means of specific examples and the present invention is by no means limited to these specific examples as is appreciated from the detailed explanation of the invention.

According to the method of the present invention, bisphenol A produced can be recovered by a known method such as the removal of phenol by evaporation or crystallization. The bisphenol A per se thus recovered may be used as the final product or it may be further subjected to other processes such as purification and forming process prior to practical use. According to a known purifying method, colorless bisphenol A having a high purity can economically and effectively be obtained by crystallizing it as a crystalline adduct with phenol and then removing the phenol.

As has been explained above in detail, according to the method of the present invention having the foregoing construction, the water generated through the reaction can rapidly be removed simultaneously with or alternatively to the reaction by a pervaporation operation and, therefore, the catalytic activity of the ion-exchange resin is not impaired at all. Moreover, any complicated operations associated with the dehydration are not required.

For this reason, the acidic ion-exchange resin catalyst can continuously be used over a long time period without any treatment for the regeneration thereof.

According to the method of the present invention, bisphenol A can thus be economically prepared from acetone and phenol in a high conversion rate and high yield as has been detailed above.

The method of the present invention will be described in more detail with reference to the following non-limitative working Examples and the effects practically achieved by the present invention will also be discussed in detail in comparison with Comparative Examples. In the following Examples and Comparative Examples, the term "part" means "part by weight" unless otherwise specified.

EXAMPLE 1

A poly(4,4'-oxydiphenylene pyromellitic acid imide) asymmetrical polyimide membrane used in this Example was produced by heat-imidation of the corresponding unsymmetrical polyamic acid.

Figure 3:
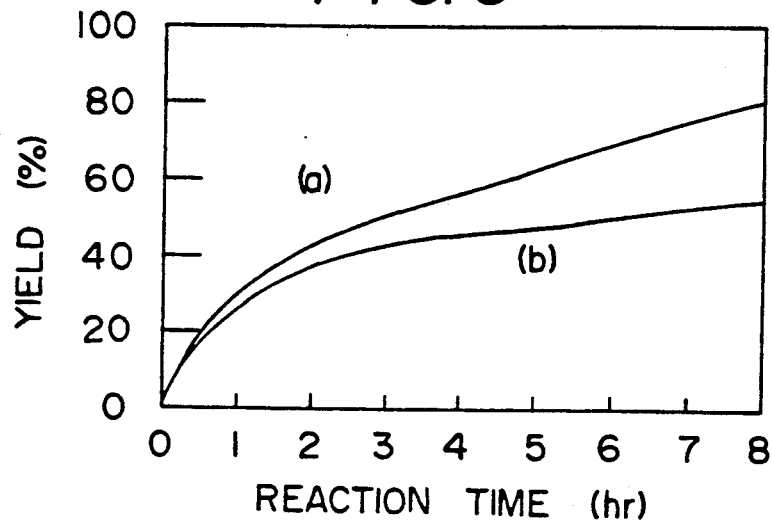
FIG. 3 shows the change in the yield of bisphenol A with time observed in Example 1 (curve (a)) and Comparative Example 1 (curve (b)).

The asymmetrical polyimide membrane produced by a phase inversion method was fitted to a reactor as shown in FIG. 1, there were charged, to the reactor, 86.4 parts of phenol, 8.9 parts of acetone and 4.7 parts of a strong acidic ion-exchange resin as a catalyst (Revachit SPC-118BG available from Bayer Co., Ltd. in which 20% of the ion-exchange groups were neutralized with mercaptoethylamine), the mixture was heated to 70° C. and a reduced pressure was applied onto the downstream side of the membrane to perform pervaporation separation. The yield of bisphenol A reached 50% after 3 hours and 80% after 8 hours as shown in FIG. 3 (curve (a)). The selectivity toward bisphenol A was 92%.

The resulting slurry of the reaction products was analyzed and it was found that a 3-nuclear compound was not detected and that the amounts of p,p'-isomers and the Dianine compound were 1.5% by weight and 0.2% by weight with respect to the amount of bisphenol A, respectively.

EXAMPLE 2

Figure 2:
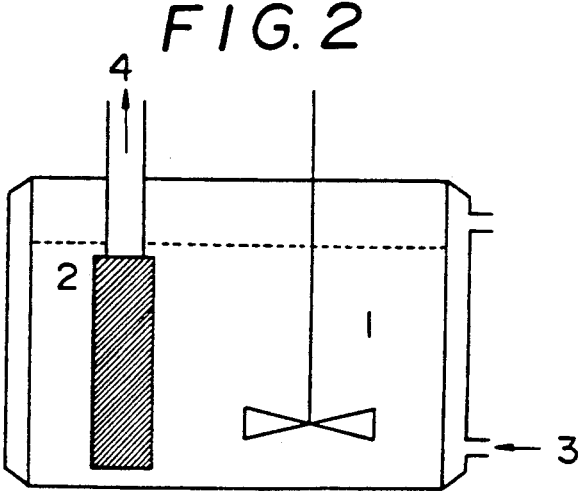

The same procedures used in Example 1 were repeated except that as a separating membrane there was used an inorganic membrane obtained by coating a porous alumina tube having a pore size of about 1 $\mu$m with an alumina membrane according to the sol-gel method and an apparatus as shown in FIG. 2 was used to perform the pervaporation separation. As a result, it was found that the yield of bisphenol A reached 50% after 2 hours and 90% after 8 hours.

EXAMPLE 3

The same procedures used in Example 2 were repeated to perform the pervaporation separation except that as a separating membrane there was used an inorganic-organic composite membrane obtained by coating a porous alumina tube with a fluorine atom-containing ion-exchange resin (available from Du Pont under the trade name of Nafion 117) and it was found that the yield of bisphenol A reached 75% after 8 hours.

COMPARATIVE EXAMPLE 1

The same procedures used in Example 1 were repeated except that separation through a membrane was not performed. As seen from FIG. 3 (curve (b)), the yield of bisphenol A was 50% after 8 hours and it was only 70% even after the reaction was further continued under the same conditions for 24 hours.

We claim:

1. A method for preparing 2,2-bis(4-hydroxyphenyl) propane comprising reacting acetone and phenol in the presence of an acidic ion-exchange resin as a catalyst wherein the reaction of acetone and phenol is performed at a temperature of from 30° to 120° C. removing a part of the water generated during the reaction from a mixed solution containing acetone and phenol by a pervaporation method with a selectively water-permeable membrane.

2. The method for preparing 2,2-bis(4-hydroxyphenyl) propane of claim 1 wherein the selectively water-permeable membrane has a water-permeation velocity ranging from 10 to 10,000 g/m$^2$ h.

3. The method for preparing 2,2-bis(4-hydroxyphenyl) propane of claim 2 wherein the selectively water-permeable membrane has a ratio of water-permeation velocity to (acetone+phenol)-permeation velocity of not less than 50.

4. The method for preparing 2,2-bis(4-hydroxyphenyl) propane of claim 1 wherein the selectively water-permeable membrane is an inorganic porous membrane.

5. The method for preparing 2,2-bis(4-hydroxyphenyl) propane of claim 4 wherein the inorganic porous membrane has a fine pore size in the order of from 20 to 10 Å.

6. The method for preparing 2,2-bis(4-hydroxyphenyl) propane of claim 4 wherein the inorganic porous membrane is at least one member selected from the group consisting of porous glass membranes, porous silica membranes, porous alumina membranes and porous ceramics membranes.

7. The method for preparing 2,2-bis(4-hydroxyphenyl) propane of claim 1 wherein the selectively water-permeable membrane is an organic polymer membrane.

8. The method for preparing 2,2-bis(4-hydroxyphenyl) propane of claim 7 wherein the organic polymer membrane is at least one member selected from the group consisting of ionized polysaccharide membranes, ion-exchange resin membranes of styrene-divinylbenzene resins or perfluoro resins, polyamide membranes, polyimide membrane, polyamidoimide membranes, polyvinyl alcohol membranes, polyvinyl acetate membranes and polyacrylonitrile membranes.

9. The method, for preparing 2,2-bis(4-hydroxyphenyl) propane of claim 8 wherein the organic polymer membrane is modified by introducing functional groups selectd from the group consisting of hydroxyl, carboxyl and sulfonic acid groups or by introducing a compound carrying functional groups selected from the above listed groups into the main chain, side chains and/or chain ends of the polymer.

10. The method for preparing 2,2-bis(4-hydroxyphenyl) propane of claim 1 wherein the selectively water-permeable membrane is an inorganic-organic composite membrane.

11. The method for preparing 2,2-bis(4-hydroxyphenyl) propane of claim 10 wherein the inorganic-organic composite membrane is at least one membrane selected from the group consisting of ionized polysaccharide membranes, ion-exchange resin membranes of styrene-divinylbenzene resins or perfluoro resins, polyamide membranes, polyimide membrane, polyamidoimide membranes, polyvinyl alcohol membranes, polyvinyl acetate membranes and polyacrylonitrile membranes, which is supported by at least one membrane selected from the group consisting of porous glass membranes, porous silica membranes, porous alumina membranes and porous ceramics membranes.

12. The method for preparing 2,2-bis(4-hydroxyphenyl) propane of claim 1 wherein the ion-exchange resin catalyst is a sulfonic acid type cation-exchange resin.

13. The method for preparing 2,2-bis(4-hydroxyphenyl) propane of claim 12 wherein the cation-exchange resin is modified and the ratio of modification of the resin ranges from 5 to 35 mole % with respect to the molar amount of the sulfonic acid groups in the resin.

14. The method for preparing 2,2-bis(4-hydroxyphenyl) propane of claim 13 wherein the cation-exchange resin is modified with a compound carrying a mercapto group in the molecule.

* * * * *

UNITED STATES PATENT AND TRADEMARK OFFICE
CERTIFICATE OF CORRECTION

PATENT NO. : 5,087,767

DATED : February 11, 1992

INVENTOR(S) : Okamoto et al.

It is certified that error appears in the above-identified patent and that said Letters Patent is hereby corrected as shown below:

In column 8, line 39, before "remov-" insert --while--.

Signed and Sealed this

Tenth Day of August, 1993

Attest:

MICHAEL K. KIRK

*Attesting Officer*     Acting Commissioner of Patents and Trademarks